(12) United States Patent
Thalacker et al.

(10) Patent No.: US 9,498,313 B2
(45) Date of Patent: Nov. 22, 2016

(54) KIT OF PARTS, METHOD OF PRODUCING AND USE THEREOF

(75) Inventors: Christoph Thalacker, Weilheim (DE);
Karsten Dede, Landsberg (DE);
(Continued)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 841 days.

(21) Appl. No.: 13/812,588

(22) PCT Filed: Jul. 26, 2011

(86) PCT No.: PCT/US2011/045354
§ 371 (c)(1),
(2), (4) Date: Jan. 28, 2013

(87) PCT Pub. No.: WO2012/015814
PCT Pub. Date: Feb. 2, 2013

(65) Prior Publication Data
US 2013/0143176 A1    Jun. 6, 2013

(30) Foreign Application Priority Data

Jul. 29, 2010  (EP) ..................................... 10171184

(51) Int. Cl.
*A61K 6/083*  (2006.01)
*A61C 19/00*  (2006.01)
(Continued)

(52) U.S. Cl.
CPC ................ *A61C 19/00* (2013.01); *A61C 5/04* (2013.01); *A61C 5/08* (2013.01); *A61C 7/16* (2013.01);
(Continued)

(58) Field of Classification Search
CPC .............................. A61K 6/083; A61K 6/0047
See application file for complete search history.

(56) References Cited

U.S. PATENT DOCUMENTS 4,259,075 A * 3/1981 Yamauchi ............... A61L 24/06
106/35
4,388,421 A * 6/1983 Suzuki ................. A61K 6/0088
260/998.11
(Continued)

FOREIGN PATENT DOCUMENTS

EP        0006757      1/1980
EP        0712622      5/1996
(Continued)

OTHER PUBLICATIONS

1507N EPO Extended Search Report for EP Application No. EP10171184, PCT/US2011/045354, mailed on Dec. 20, 2010, pp. 1-8.
(Continued)

*Primary Examiner* — Michael Pepitone (57) ABSTRACT

The present disclosure relates to a kit of parts comprising part A and part B, part A comprising a polymerizable component having an acid group in the molecule, an initiator, part B comprising an activator, and a film former with a molecular weight of at least 1000. The present disclosure also relates to a composition obtainable by mixing the components contained in the kit of parts and to a process for producing the kit of parts comprising the steps of bringing the components contained in part B of the kit in contact with a surface, drying the surface to form a film.

11 Claims, 1 Drawing Sheet

(75) Inventors: Alexandra Glaser, Seefeld (DE);
Thomas Luchterhandt, Pleidelsheim (DE); Markus Watermann, Inning am Ammersee (DE)

(51) Int. Cl.
*A61K 6/087* (2006.01)
*A61C 5/04* (2006.01)
*A61C 5/08* (2006.01)
*A61C 7/16* (2006.01)
*A61C 13/271* (2006.01)
*A61K 6/00* (2006.01)

(52) U.S. Cl.
CPC .............. *A61C 13/26* (2013.01); *A61K 6/0017* (2013.01); *A61K 6/0023* (2013.01); *A61K 6/083* (2013.01); *A61K 6/087* (2013.01); *A61K 6/0835* (2013.01); *A61K 6/0047* (2013.01)

(56) References Cited

U.S. PATENT DOCUMENTS

| | | |
|---|---|---|
| 4,499,251 A | 2/1985 | Omura |
| 4,537,940 A | 8/1985 | Omura |
| 4,539,382 A | 9/1985 | Omura |
| 4,872,936 A | 10/1989 | Engelbrecht |
| 5,130,347 A | 7/1992 | Mitra |
| 5,151,479 A * | 9/1992 | Mukai .................. A61K 6/0023 523/109 |
| 5,332,429 A | 7/1994 | Mitra |
| 5,525,647 A | 6/1996 | Eichmiller |
| 5,530,038 A | 6/1996 | Yamamoto |
| 5,998,495 A | 12/1999 | Oxman |
| 6,025,406 A | 2/2000 | Oxman |
| 6,030,606 A | 2/2000 | Holmes |
| 6,043,295 A | 3/2000 | Oxman |
| 6,071,983 A † | 6/2000 | Yamamoto |
| 6,084,004 A | 7/2000 | Weinmann |
| 6,105,761 A | 8/2000 | Peuker |
| 6,187,833 B1 | 2/2001 | Oxman |
| 6,288,138 B1 | 9/2001 | Yamamoto |
| 6,387,981 B1 | 5/2002 | Zhang |
| 6,444,725 B1 | 9/2002 | Trom |
| 6,450,717 B1 | 9/2002 | Salz |
| 6,458,868 B1 | 10/2002 | Okada |
| 6,528,555 B1 | 3/2003 | Nikutowski |
| 6,572,693 B1 | 6/2003 | Wu |
| 6,765,036 B2 | 7/2004 | Dede |
| 6,899,948 B2 | 5/2005 | Zhang |
| 6,939,900 B2 | 9/2005 | Ario |
| 6,960,079 B2 | 11/2005 | Brennan |
| 6,982,288 B2 | 1/2006 | Mitra |
| 7,097,075 B2 | 8/2006 | Peuker |
| 7,816,423 B2 | 10/2010 | Karim |
| 8,404,144 B2 | 3/2013 | Abuelyaman |
| 2003/0008967 A1 | 1/2003 | Hecht |
| 2005/0281757 A1 | 12/2005 | Ibrahim |
| 2008/0206712 A1 | 8/2008 | Kennard |
| 2010/0129777 A1 | 5/2010 | Ziegler |

FOREIGN PATENT DOCUMENTS

| | | |
|---|---|---|
| EP | 0923924 | 6/1999 |
| EP | 1051961 | 11/2000 |
| JP | 63250310 | 10/1988 |
| WO | WO 2004-032785 | 4/2004 |
| WO | WO 2007-121160 | 10/2007 |
| WO | WO 2012-015814 | 2/2012 |

OTHER PUBLICATIONS

International Search Report for International Application No. PCT/US2011/045354, mailed on Oct. 5, 2011, 4 pages.

* cited by examiner
† cited by third party

KIT OF PARTS, METHOD OF PRODUCING AND USE THEREOF

CROSS REFERENCE TO RELATED APPLICATIONS

This application is a national stage filing under 35 U.S.C. 371 of International Application No. PCT/US2011/045354, filed Jul. 26, 2011, which claims priority to European Application No. 10171184.4, filed Jul. 29, 2010. The disclosures of both applications are incorporated by reference in their entirety herein.

FIELD OF THE INVENTION

The invention relates to a kit of parts comprising at least two parts, wherein one part comprises an activator and a film former. The kit of parts can be used in the dental field, especially for producing an adhesive to be applied to the surface of a tooth.

BACKGROUND ART

Adhesives can be produced and applied to the surface of a tooth in various ways.

EP 0 006 757 (Loctite) relates to a dental mixing tool for catalyzed two-part compositions and method for catalyzing said compositions.

U.S. Pat. No. 5,525,647 (American Dental Association) relates to a method and device for controllably affecting the reaction of dental adhesives.

U.S. Pat. No. 6,288,138 (Sun Medical) mentions an adhesive kit comprising a powdery or granular sulfinic acid or salt thereof or barbituric acid derivative adhered or absorbed to an applicator.

U.S. Pat. No. 6,450,717 (Ivoclar) refers to an applicator kit for applying a substance formed of a reaction substance and a fluid.

US 2010/0129777 (Ernst Mühlbauer) describes a kit for fixing a dental restoration material on a tooth substance. The kit contains the a) an electron-donating compound, b) a first adhesive component and c) a second adhesive component. The first and/or second adhesive component may exhibit HEMA.

U.S. Pat. No. 5,151,479 (Mukai) relates to a dental adhesive composition containing a) a certain aliphatic amine salt of a polymerizable phosphoric ester, at least one radial-polymerizable unsaturated monomer, such as HEMA, and c) a radical polymerization initiator.

However, there is still room for improvement especially with regard to the requirements to be fulfilled with respect to modern dental materials.

DESCRIPTION OF THE INVENTION

An object which can be addressed by the invention is the provision of a kit of parts which facilitates the production and application of an adhesive composition.

In particular, a kit of parts can be provided which allows for a consecutive application of an adhesive composition to different surfaces, without a significant drop in performance.

In one embodiment, the invention is directed to a kit of parts comprising part A and part B, part A comprising
    a polymerizable component having an acid group in the molecule,
    an initiator, part B comprising
    activator, and
    film former.

In another embodiment the present invention features a composition obtainable by mixing the components contained in the kit.

A further aspect of the invention is directed to a method for producing the kit as described in the text of the invention, the method comprising the steps of bringing the components contained in part B of the kit in contact with a surface and drying the surface to form a film.

DEFINITIONS

Within the description of the invention, the following terms are defined as follows:

The term "visible light" is used to refer to light having a wavelength of about 400 to about 800 nanometers (nm).

A "dental composition" is any composition which can be used in the dental field or orthodontic area. In this respect the composition should be not detrimental to the patients' health and thus free of hazardous and toxic components being able to migrate out of the composition. Examples of dental compositions include permanent and temporary crown and bridge materials, artificial crowns, anterior or posterior filling materials, adhesives, mill blanks, lab materials and orthodontic devices.

Dental compositions are typically hardenable compositions, which can be hardened at ambient conditions, including a temperature range from about 15 to about 50° C. or from about 20 to about 40° C. within a time frame of about 30 min or about 20 min or about 10 min.

Higher temperatures are not recommended as they might cause pain to the patient and may be detrimental to the patient's health.

Dental compositions are typically provided to the practitioner in comparable small volumes, that is volumes in the range from about 0.05 to about 100 ml or from about 0.1 to about 50 ml or from about 0.2 to about 10 ml or from about 0.5 to about 2 ml.

A "monomer" is any chemical substance which can be characterized by a chemical formula, bearing polymerizable groups (including (meth)acrylate groups) which can be polymerized to oligomers or polymers thereby increasing the molecular weight. The molecular weight of monomers can usually simply be calculated based on the chemical formula given.

A "hardenable compound or material" is any compound which can be cured or solidified e.g. by heating to cause polymerization, chemical crosslinking, radiation-induced polymerization or crosslinking or using a redox initiator. A hardenable compound may contain only one, two, three or more polymerizable groups. Typical examples of polymerizable groups include epoxy groups and unsaturated carbon groups, such as a vinyl group being present i.a. in a (methyl)acrylate group.

A "resin" contains all hardenable compounds (monomers, oligomers and/or polymers) being present in the hardenable composition. The resin may contain only one hardenable compound or a mixture of different hardenable compounds.

A "film former" is a substance which will cause a composition containing it to change from a liquid stage to a solid stage in such a manner as to form a film or coating on a surface. A definition of the term "film former" can also be found in DIN 55945 (1999-07-00). A film former is typically part of a binder system. The term "film former" is often used in varnishes. The substance hydroxyethyl methacrylate (HEMA) cannot be regarded as a film former according to this definition.

A "film" is a thin sheet or strip of a preferably flexible material. A coating of a surface with a material typically results in a film.

A "filler" contains all fillers being present in the hardenable composition. Either only one type of filler or a mixture of different fillers can be used.

"Dispersed within the resin" means that filler particles are present in the resin at a homogeneous concentration throughout the resin.

A "nano-sized filler" is a filler, the individual particles thereof have a size in the region of nanometers, e.g. an average particle diameter of less than about 200 nm. Useful examples are given in U.S. Pat. No. 6,899,948 and U.S. Pat. No. 6,572,693, the content of which especially with regard to nano-sized silica particles is herein incorporated by reference.

A "curing, hardening or setting reaction" is used interchangeably and refers to a reaction wherein physical properties such as viscosity and hardness of a composition changes over the time due to a chemical reaction between the individual components.

An "ethylenically unsaturated acidic compound" in the context of the invention is meant to include monomers, oligomers, and polymers having ethylenic unsaturation and acid and/or acid-precursor functionality. Acidic-precursor functionalities include, e.g. anhydrides, acid halides and pyrophosphates. The acidic group preferably comprises one or more carboxylic acid residues, such as —COOH or —CO—O—CO—, phosphoric acid residues, such as —O—P(O)(OH)OH, or sulfonic acid residues, such as —SO3H.

An "initiator" in the context of the invention is a substance being able to catalytically initiate a chemical reaction, preferably via a free radical reaction. The initiator can be a single compound or can comprise more than one component, such as a combination of a sensitizing agent with a reducing agent. Depending on the reaction conditions chosen (e.g. pH-value >7 or pH-value <7) different initiators can be preferred.

A mixture or solution is considered to be "homogeneous" in the context of the invention, if it appears clear to the human eye, and essentially no settling of the filler or separation of components can be visually detected within a given time period (e.g. 24 hours after preparation of the composition). In addition, this can be proven by analysing the particle size distribution of the composition. A dispersion or mixture is considered to be "homogeneous", if the particle size of the particles in 50% of the analysed volume is in a range below about 1 µm, wherein the particle size distribution is measured as described in the text below.

A "dispersion" is a homogeneous mixture of different components, especially the distribution of solid particles in a liquid. If only liquid components are concerned and no solid particles are present, the mixture can also be classified as emulsion. If the size of the solid particles is very low, such that the presence of individual particles cannot be identified by the human eye, a dispersion sometimes looks like a clear or slightly cloudy solution.

As used herein "adhesive" or "dental adhesive" refers to a composition used as a pre-treatment on a dental structure (e.g., a tooth) to adhere a "dental material" (e.g., a "restorative", an orthodontic appliance (e.g., bracket), or an "orthodontic adhesive") to the dental structure. An "orthodontic adhesive" refers to a composition used to adhere an orthodontic appliance to a dental structure (e.g., tooth) surface. Generally, the dental structure surface is pre-treated, e.g., by etching, priming, and/or applying an adhesive to enhance the adhesion of the "orthodontic adhesive" to the dental structure surface.

As used herein, a "self-etching" composition refers to a composition which bonds to a dental structure surface without pretreating the dental structure surface with an etchant. Preferably, a self-etching composition can also function as a self-primer wherein no separate etchant or primer are used.

As used herein, a "self-adhesive" composition refers to a composition that is capable of bonding to a dental structure surface without pretreating the dental structure surface with a primer or bonding agent. Preferably, a self-adhesive composition is also a self-etching composition wherein no separate etchant is used.

As used herein, "hardening" or "curing" a composition are used interchangeably and refer to polymerisation and/or crosslinking reactions including, for example, photopolymerization reactions and chemical polymerization techniques (e.g., ionic reactions or chemical reactions forming radicals effective to polymerize ethylenically unsaturated compounds) involving one or more materials included in the composition.

As used herein, a "dental structure surface" refers to tooth structures (e.g., enamel, dentin, and cementum) and bone.

As used herein, an "untreated" dental structure surface refers to a tooth or bone surface that has not been treated with an etchant, primer, or bonding agent prior to application of a self-etching adhesive or a self-adhesive composition of the present invention.

As used herein, an "unetched" dental structure surface refers to a tooth or bone surface that has not been treated with an etchant prior to application of a self-etching adhesive or a self-adhesive composition of the present invention.

As used herein, an "etchant" refers to an acidic composition that is capable of fully or partially solubilizing (i.e., etching) a dental structure surface. The etching effect can be visible to the naked human eye and/or instrumentally detectably (e.g., by light microscopy). Typically, an etchant is applied to the dental structure surface for a period of about 10 to 30 s.

As used herein, "dental material" refers to a material that may be bonded to a dental structure surface and includes, for example, dental restoratives, orthodontic appliances, and/or orthodontic adhesives.

As used herein, a "chemically stable" composition refers to a composition that has a shelf-life of at least one year, and preferably at least 2 years, at refrigeration (e.g., at a temperature below about 10° C. or below about 5° C.). Shelf-life of a self-adhesive composition is typically measured by determining if the aged composition provides acceptable bond strengths when the aged composition is bonded to a dental structure surface.

As used herein, "(meth)acryl" is a shorthand term referring to "acryl" and/or "methacryl". For example, a "(meth) acryloxy" group is a shorthand term referring to either an acryloxy group (i.e., CH2=CH—C(O)—O—) and/or a methacryloxy group (i.e., CH2=C(CH3)-C(O)—O—).

A "derivative" is a chemical compound showing a chemical structure closely related to the corresponding reference compound and containing all featured structural elements of the corresponding reference compound but having small modifications like bearing in addition comparably small additional chemical groups like e.g. $CH_3$, Br, Cl, or F or not bearing comparably small chemical groups like e.g. $CH_3$ in comparison to the corresponding reference compound. The following examples might illustrate this: tetramethyl bis-phenol A bearing four additional methyl groups with respect to the reference compound bis-phenol A, and bis-phenol F not bearing two additional methyl groups with respect to the reference compound bis-phenol A are derivatives of bis-phenol A within the meaning of this definition. Likewise, compounds bearing alkyl chains of different length are derivatives within the meaning of this definition.

"Ambient conditions" mean the conditions which the inventive composition is usually subjected to during storage and handling. Ambient conditions may, for example, be a pressure of about 900 to about 1100 mbar, a temperature of about −10 to about 60° C. and a relative humidity of about 10 to about 100%. In the laboratory ambient conditions are typically adjusted to about 23° C. and a relative humidity of about 50%. In the dental and orthodontic field ambient conditions are reasonably understood as a pressure of about 950 to about 1050 mbar, temperature of about 15 to about 40° C. and relative humidity of about 20 to about 80%.

As used herein, "a", "an", "the", "at least one" and "one or more" are used interchangeably. The terms "comprises" or "contains" and variations thereof do not have a limiting meaning where these terms appear in the description and claims. Also herein, the recitations of numerical ranges by endpoints include all numbers subsumed within that range (e.g., 1 to 5 includes 1, 1.5, 2, 2.75, 3, 3.80, 4, 5, etc.).

Unless otherwise indicated, all numbers expressing quantities of ingredients, measurement of properties such as contrast ratio and so forth used in the specification and claims are to be understood as being modified in all instances by the term "about." Any numerical value, inherently contains certain errors necessarily resulting from the standard deviations found in their respective testing measurements.

DETAILED DESCRIPTION OF THE INVENTION

Generally, the invention relates to a kit of parts, wherein one part comprises an activator and a film former. Such a kit is especially suitable in the dental and orthodontic area.

In contrast to current commercial products, where an activator is applied to bristles of an application device in granular form, according to the invention the activator is applied together with a film former.

The kit can be used for producing an adhesive composition suitable for securing of a (e.g. dental or orthodontic) redox or dual curing (i.e. redox and radiation curing) material, e.g. a cement, filling composite or orthodontic adhesive.

The invention can be beneficial for the practitioner in a couple of aspects.

Using or adding a film former in combination with an activator typically facilitates the production of thin films and a homogeneous coating of the activator on various surfaces.

A further advantage can be seen in the fact that this facilitates the provision of a durable coating that is, the activator cannot simply fall off the surface of the application device as it has been observed when granules are attached to the bristles of an applicator brush.

In application devices according to the prior art the activator can easily be lost or detached from the bristles under the influence of mechanical stress, e.g. during transportation, but also during the application of the adhesive by rubbing it on the tooth surface.

Moreover, if several teeth have to be treated in a consecutive way, most of the activator is lost from the application device during treatment of the first tooth, and bond strength to the later teeth is impaired, if an application device according to the prior art is used.

This can be detrimental, if e.g. dental bridges have to be cemented on two or more core preparations, or if several dental restorations have to be placed at the same time.

This issue can be overcome, if the kit according to the invention is used.

It was found that the activator (having been dissolved or dispersed in the film former) resolves slowly but in sufficient amount so that several applications of the adhesive composition can be accomplished.

If the kit is used in the dental or orthodontic area, several teeth can be treated consecutively with the same application device, without a significant drop in bond strength.

According to a preferred embodiment, the kit described in the present text is not only suitable to be used in the dental and/or orthodontic area, but indeed to be used in these areas or for use in these areas. These kinds of products are typically provided to the practitioner with an instruction for use. So, the kit may also comprise an instruction for use. Possible process steps are described later in the description.

One embodiment of the present invention is directed to a kit of parts comprising at least 2 parts, part A and part B. Each part typically comprises one or more components.

When providing the kit of parts it should—if possible—be avoided to combine components within a part, components, which may chemically react with each other thereby forming an undesired product, especially during storage of the kit of parts.

Thus, the kit of parts typically is provided in a manner, where those reactive components are separated from each other, at least during storage in order to avoid an undesired reaction.

However, when used, the components being present in the individual parts are combined, wherein at least some of the components typically chemically react with each other. Such a reaction includes a polymerization reaction, which is typically started by combining a suitable initiator and a polymerizable monomer. When the components being present in part A and part B are (at least partially) combined, a hardenable composition is typically obtained.

The kit comprises a polymerizable monomer having at least one acidic group in the molecule. This component is hereinafter referred to as component (A1).

If desired, different components falling within the definition of component (A1) can be present in the composition, which can be obtained when the components being present in part A and part B of the kit are combined.

Component (A1) can be characterized by at least one of the following features:
  Molecular weight (Mw): from about 70 to about 700 g/mol or from about 100 to about 600 or from about 200 to about 500 g/mol,
  Viscosity: from about 0.1 to about 10 Pa*s, or from about 0.2 to about 5 Pa*s or from about 0.5 to about 2 Pa*s measured at 23° C.,
  Refractive index: from about 1.42 to about 1.55 (nD).

Component (A1) comprises a polymerizable moiety and an acidic moiety.

Examples of the polymerizable moiety include acrylate, (meth)acrylate and epoxy-functional moieties.

Examples of the acidic moiety include carboxylic acid residues, phosphoric acid residues, or sulphonic acid residues.

Using a component (A1) with at least one of the following features was found to be beneficial, especially, if the hardenable composition should show sufficient adhesiveness:

polymerizable moiety comprising a (meth)acrylate group,
acidic moiety comprising a phosphor, carbon or sulphur containing group,
molecular weight being in the range from about 70 to about 700 or from about 100 to about 600 or from about 200 to about 500 g/mol.

In one embodiment, the polymerizable monomer having an acid group in the molecule can be represented by formula (I)

$$A_n\text{-}B\text{--}C_m \quad (I)$$

with A being an ethylenically unsaturated group, such as a (meth)acryl moiety,

B being a spacer group, such as (i) linear or branched C1 to C12 alkyl, optionally substituted with OH, (ii) C6 to C12 aryl, optionally substituted with OH, (iii) organic group having 4 to 20 carbon atoms bonded to one another by one or more ether, thioether, ester, thioester, thiocarbonyl, amide, urethane, carbonyl and/or sulfonyl linkages, each optionally substituted with OH, and C being an acidic group, with m, n=1, 2, 3, 4, 5 or 6, wherein the acidic group comprises one or more carboxylic acid residues, such as —COOH or —CO—O—CO—, phosphoric acid residues, such as —O—P(O)(OH)OH, or sulphonic acid residues, such as —SO3H.

Specific examples of ethylenically unsaturated acidic compounds as component (A1) include, but are not limited to glycerol phosphate mono(meth)acrylates, glycerol phosphate di(meth)acrylates, hydroxyethyl (meth)acrylate (e.g., HEMA) phosphates, bis((meth)acryloxyethyl) phosphate, ((meth)acryloxypropyl) phosphate, bis((meth)acryloxypropyl) phosphate, bis((meth)acryl-oxy)propyloxy phosphate, (meth)acryloxyhexyl phosphate, bis((meth)acryloxyhexyl) phosphate, (meth)acryloxyoctyl phosphate, bis((meth)acryloxyoctyl) phosphate, (meth)acryloxydecyl phosphate, bis((meth)acryloxydecyl) phosphate, caprolactone methacrylate phosphate, citric acid di- or tri-methacrylates, poly (meth)acrylated oligomaleic acid, poly(meth)acrylated polymaleic acid, poly(meth)acrylated poly(meth)acrylic acid, poly(meth)acrylated polycarboxyl-polyphosphonic acid, poly(meth)acrylated polychlorophosphoric acid, poly (meth)acrylated polysulfonate, poly(meth)acrylated polyboric acid, and the like. Also monomers, oligomers, and polymers of unsaturated carboxylic acids such as (meth)acrylic acids, aromatic (meth)acrylated acids (e.g., methacrylated trimellitic acids), and anhydrides thereof can be used.

Some of these compounds can be obtained, e.g., as reaction products between isocyanatoalkyl (meth)acrylates and carboxylic acids. Additional compounds of this type having both acid-functional and ethylenically unsaturated components are described in U.S. Pat. No. 4,872,936 (Engelbrecht) and U.S. Pat. No. 5,130,347 (Mitra). A wide variety of such compounds containing both the ethylenically unsaturated and acid moieties can be used. If desired, mixtures of such compounds can be used.

Additionally, ethylenically unsaturated compounds with acid functionality include, for example, polymerizable bisphosphonic acids as disclosed for example, in U.S. Provisional Application No. 60/437,106, filed Dec. 30, 2002; AA:ITA:IEM (copolymer of acrylic acid:itaconic acid with pendent methacrylate made by reacting AA:ITA copolymer with sufficient 2-isocyanatoethyl methacrylate to convert a portion of the acid groups of the copolymer to pendent methacrylate groups as described, for example, in Example 11 of U.S. Pat. No. 5,130,347 (Mitra)); and those recited in U.S. Pat. No. 4,259,075 (Yamauchi et al.), U.S. Pat. No. 4,499,251 (Omura et al.), U.S. Pat. No. 4,537,940 (Omura et al.), U.S. Pat. No. 4,539,382 (Omura et al.), U.S. Pat. No. 5,530,038 (Yamamoto et al.), U.S. Pat. No. 6,458,868 (Okada et al.), and EP 0 712 622 A1 (Tokuyama Corp.) and EP 1 051 961A1 (Kuraray Co., Ltd.).

Typical compositions also include an ethylenically unsaturated acidic compound with at least one phosphoric acid group (e.g. P—OH moiety).

Examples of preferred phosphoric acid group-containing polymerizable monomer include e.g. 2-(meth)acryloyloxyethyl dihydrogenphosphate, bis[2-(meth)acryloyloxyethyl] hydrogenphosphate, 2-(meth)acryloyloxyethylphenyl hydrogen phosphate, 6-(meth)acryloyloxyhexyl dihydrogen-phosphate, 6-(meth)acryloyloxyhexylphenyl hydrogenphosphate, 10-(meth)acryloyloxydecyl dihydrogenphosphate, 1,3-di(meth)acryloyloxypropane-2-dihydrogenphosphate, 1,3-di(meth)-acryloyloxypropane-2-phenyl hydrogenphosphate, and bis[5-{2-(meth) acryloyloxyethoxy-carbonyl}heptyl]hydrogenphosphate.

Component (A1) is typically present in the part A of the kit of parts in an amount of at least about 2 wt.-% or at least about 5 wt.-% or at least about 10 wt.-%.

The amount of component (A1) being present in part A of the kit of parts is typically up to about 20 wt.-% or up to about 30 wt.-% or up to about 40 wt.-%.

Typical ranges include from about 2 to about 40 or from about 5 to about 30 or from about 10 to about 20 wt.-%.

Besides the polymerizable component having an acid group in the molecule (A1), the composition may comprise a further polymerizable component (A2) being different from compound (A1). Component (A2) can be a freeradically polymerizable material, including ethylenically unsaturated monomer, monomers or oligomers or polymers.

Examples of ethylenically unsaturated compound being different from compound (A1) as component (A2) are compounds, which e.g. do not comprise an acidic group.

Examples for component (A2) include, but are not limited to ethylene glycol di(meth)acrylate, diethylene glycol di(meth)acrylate, triethylene glycol di(meth)acrylate, tetraethylene glycol di(meth)acrylate, polyethylene glycol di(meth)acrylate, 1,3-butylene glycol di(meth)acrylate, 1,6-hexane diol di(meth)acrylate, neopentyl glycol di(meth) acrylate, tripropylene glycol di(meth)acrylate, polypropylene glycol di(meth)acrylate, glycerol di(meth)acrylate, bisphenol A di(meth)acrylate, bisphenol A glycidyl di(meth) acrylate, bisphenol A propyl di(meth)acrylate, bisphenol A isopropyl di(meth)acrylate, ethylene oxide modified bisphenol A di(meth)acrylate, ethylene oxide modified bisphenol A glycidyl di(meth)acrylate, 2,2-bis(4-methacryloxypropoxyphenyl)propane, 7,7,9-trimethyl-4,13-dioxy-3,14-dioxa-5, 12-diazahexadecane-1,16-diol di(meth)acrylate, neopentyl glycol hydroxypivalic acid ester di(meth)acrylate, caprolactone modified hydroxypivalic acid neopentyl glycol ester di(meth)acrylate, trimethylol ethane di(meth)acrylate, trimethylol propane di(meth)acrylate, trimethylol methane tri (meth)acrylate, trimethylol ethane tri(meth)acrylate, trimethylol propane tri(meth)acrylate, pentaerythritol tri(meth) acrylate, dipentaerythritol tri(meth)acrylate, pentaerythritol tetra(meth)acrylate, dipentaerythritol tetra(meth)acrylate, dipentaerythritol hexa(meth)acrylate, the reaction product of 3-chloro-2-hydroxypropyl (meth)acrylate and methylcyclohexane diisocyanate, the reaction product of 2-hydroxypropyl (meth)acrylate and methylcyclohexane diisocyanate, the reaction product of 2-hydroxypropyl (meth)acrylate and methylene bis(4-cyclohexylisocyanate), the reaction product of 2-hydroxypropyl(meth)acrylate and trimethylhexamethylene diisocyanate, the reaction product of 2-hydroxyethyl (meth)acrylate and isophorone diisocyanate, and the reaction product of 3-chloro-2-hydroxypropyl (meth)acrylate and isophorone diisocyanate, methyl (meth)acrylate, ethyl (meth)acrylate, propyl methacrylate, isopropyl methacrylate, n-butyl (meth)acrylate, iso-butyl (meth)acrylate, 2-ethylhexyl (meth)acrylate, lauryl (meth)acrylate, tridecyl (meth)acrylate, stearyl (meth)acrylate, cyclohexyl (meth) acrylate, benzyl (meth)acrylate, 2-hydroxyethyl (meth)acrylate, 2-hydroxypropyl (meth)acrylate, glycidyl (meth)acrylate, tetrahydrofurfuryl (meth)acrylate, allyl (meth)acrylate, 2-ethoxyethyl (meth)acrylate, methoxydiethylene glycol (meth)acrylate, methoxytetraethylene glycol(meth)acrylate, methoxypolyethylene glycol(meth)acrylate, phenoxy-diethyleneglycol(meth)acrylate, phenoxyhexaethyleneglycol (meth)acrylate, glycerol(meth)acrylate, tetrahydrofurfuryl (meth)acrylate, dicyclopentenyl (meth)acrylate, isobornyl (meth)acrylate, phenyl (meth)acrylate, pentaerythritol mono (meth)acrylate, dipentaerythritol mono(meth)acrylate, and mixtures thereof.

Other examples of ethylenically unsaturated compound being different from compound (A1) as component (A2) include, but are not limited to (meth)acrylate functionalized copolymers of acrylic acid, (meth)acrylic acid, maleic acid, and itaconic acid as described e.g. in U.S. Pat. No. 5,130,347. This document is explicitly mentioned and its disclosure, especially the disclosure relating to the preparation of (meth)acrylate functionalized copolymers of acrylic acid, (meth)acrylic acid, maleic acid, and itaconic acid disclosed in the above mentioned location, is regarded as being part of the disclosure of the present invention.

Examples of prepolymers according to component (A2) can be found in US 2003/008967 A1. This document is explicitly mentioned also and its disclosure, especially the disclosure relating to the preparation of unsaturated urethane prepolymers disclosed in the above mentioned location, is regarded as being part of the disclosure of the present invention. The prepolymers preferably do not contain hydroxy, acidic or ionic groups.

The urethane prepolymers as an example for the unsaturated prepolymers according to component (A2) can be obtained by reaction of (A) about 15 to about 85 wt.-% of one or more α,ω-terminated poly(meth)acrylate diols, (B) about 0 to about 30 wt.-% of one or more radically curable, polyhydroxy-functional compounds, (C) about 14 to about 60 wt.-% of one or more polyisocyanates, (D) about 1 to about 40 wt. % or a monofunctional compound, reactive vis-à-vis isocyanate groups, which contain one or more radically curable groupings.

The prepolymers obtained can have an average molecular weight (Mw) according to GPC measurements against polystyrene standards in the range between about 400 to about 200.000 g/mol, preferably between about 500 to about 100.000 g/mol and more preferably between about 600 to about 20.000 g/mol.

Generally, it is possible to use the above-mentioned monomers, polymers, and prepolymers alone or as a mixture of two or more of any of these compounds.

Part A of the kit also comprises an initiator or an initiator system as component (B) or part of component (B). The initiator or initiator system is able to initiate a hardening reaction of the polymerizable components (e.g. A1 and A2).

If desired, different components falling within the definition of component (B) can be present in the composition, which can be obtained when the components being present in part A and part B of the kit are combined.

Examples for initiators according to component (B) include, but are not limited to photo initiator systems for free radical polymerization. Typical examples are combinations of a sensitizing agent with a reducing agent.

Using a photo initiator can be beneficial, as it allows initiating the hardening process on demand, e.g. by application of light having a suitable wavelength.

The initiator or initiator system typically comprises at least one of the following elements: oxidizing agent, a reducing agent, a sensitizing agent, onium salt, electron donor or a combination of two or more of these elements.

As sensitizing agent, those which contribute to the hardening process of the polymerizable monomer by the action of a visible light having a wavelength of from about 390 nm to about 830 nm are preferred.

Examples thereof include camphorquinone, 1-phenyl propane-1,2-dione, benzil, diacetyl, benzyl dimethyl ketal, benzyl diethyl ketal, benzyl di(2-methoxyethyl) ketal, 4,4,'-dimethylbenzyl dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropyl thioxanthone, 2-nitrothioxanthone, 2-methyl thioxanthone, 2,4-dimethyl thioxanthone, 2,4-diethyl thioxanthone, 2,4-diisopropyl thioxanthone, 2-chloro-7-trifluoromethyl thioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylamino-phenyl)ketone, 4,4,'-bisdiethylaminobenzophenone, acyl phosphine oxides such as (2,4,6-trimethylbenzoyl)diphenylphosphine oxide, and azide-containing compounds. These compounds may be used singly or in admixture.

As reducing agent, tertiary amines and the like can be used. Suitable examples of the tertiary amines include N,N-dimethylaminoethyl methacrylate, ethyl 4-dimethylaminobenzoate, methyl 4-dimethylaminobenzoate, triethanolamine, N,N-dimethyl-p-toluidine, and isoamyl 4-dimethylaminobenzoate. Other reducing agents, like sodium sulfinate derivatives and organometallic compounds can be used, as well. These compounds may be used singly or in admixture.

Moreover, ternary photopolymerization initiating systems comprising a sensitizing agent, an electron donor and an onium salt can be used. Typical examples are described in U.S. Pat. No. 6,187,833, U.S. Pat. No. 6,025,406, U.S. Pat. No. 6,043,295, U.S. Pat. No. 5,998,495, U.S. Pat. No. 6,084,004 and U.S. patent application Ser. No. 10/050,218.

It is also possible to use a quadruple photopolymerization initiating system comprising two different sensitizing agents and two different reducing agents.

Other useful initiators comprise oxidizing agents such as persulfates (e.g., sodium, potassium, ammonium, and alkyl ammonium persulfates). Another preferred class of oxidizing agents includes peroxides or peroxide salts (e.g., hydrogen peroxide, benzoyl peroxide, and hydroperoxides including, for example cumene hydroperoxide, tert-butyl hydroperoxide, tert-amyl hydroperoxide, and 2,5-dihydroperoxy-2,5-dimethylhexane). Other preferred oxidizing agents include salts of cobalt (III) and iron (III), perboric acid and its salts, and salts of a permanganate anion.

Combinations of any of the above mentioned oxidizing agents can also be used. These oxidizing agents can interact with reducing agents including, for example, amines (e.g., aromatic amines), ascorbic acid, metal complexed ascorbic acid, cobalt (II) chloride, ferrous chloride, ferrous sulfate, hydrazine, hydroxylamine, oxalic acid, thiourea, and salts of dithionite, thiosulfate, benzene sulfinate, or sulfite anions.

Part B of the kit also comprises an activator, especially an activator being able to facilitate the hardening reaction of the polymerizable components. Hereinafter, the activator is referred to as component (C).

Component (C) comprises a moiety suitable of being activated either via a redox-reaction (exchange of electrons) or a photochemical reaction (absorption of light). This reaction can take place by interaction with the initiator or initiator components being present in component (B).

If desired, different components falling within the definition of component (C) can be present in the final composition obtainable when the components being present in part A and part B of the kit are combined.

The activator typically comprises at least one of the following moieties: barbituric acid, barbituric acid salt, thiobarbituric acid, thiobarbituric acid salt, sulfinic acid, sulfinic acid salt or sulfinic acid ester and derivatives thereof.

The molecular weight (Mw) of the activator is typically from about 140 to about 400.

Component (C) is typically present in part B of the kit in an amount of at least about 5 wt.-% or at least about 10 wt.-% or at least about 20 wt.-%.

The amount of component (C) being present in part B of the kit of parts is typically up to about 50 wt.-% or up to about 40 wt.-% or up to about 30 wt.-%.

Typical ranges include from about 5 to about 50 or from about 10 to about 40 or from about 20 to about 30 wt.-%.

Component (C) may comprises a sulfinic acid compound and/or mixtures thereof of the general formula

R1SOO—R2 wherein R1 is an alkyl (e.g. C1 to C18), substituted alkyl (e.g. C3 to C18), alkenyl (e.g. C2 to C18), cycloalkyl (e.g. C6 to C10), substituted cycloalkyl (e.g. C7 to C18), arylalkyl (e.g. C7 to C18), aryl or substituted aryl radical (e.g. C6 to C18) and R2 is H, metal such as Li, Na or K or is an alkyl, substituted alkyl, alkenyl, cycloalkyl, substituted cycloalkyl, arylalkyl, aryl or substituted aryl radical (e.g. C1 to C18).

If one of the radicals R1 or R2 is an unsubstituted alkyl then this radical can be a straight-chain or a branched chain and can contain, for example, from 1 to 18 carbon atoms, preferably from 1 to 10, and in particular from 1 to 6 carbon atoms. Examples of low-molecular alkyl radicals are methyl, ethyl, propyl, isopropyl, n-butyl, t-butyl, isobutyl, n-pentyl, and isoamyl.

If one of the radicals R1 or R2 is a substituted alkyl radical then the alkyl moiety of this radical preferably has the number of carbon atoms indicated above for unsubstituted alkyl.

If one of the radicals R1 or R2 is alkoxyalkyl or alkoxycarbonylalkyl then the alkoxy radical contains, for example, from 1 to 5 carbon atoms and is preferably methyl, ethyl, propyl, isopropyl, n-butyl, t-butyl, isobutyl, n-pentyl or isoamyl. If one of the radicals R1 or R2 is haloalkyl then the halo moiety is understood to be F, Cl, Br or I.

If one of the radicals R1 or R2 is alkenyl then preference is given to C3 to C5 alkenyl radicals, especially allyl.

If one of the radicals R1 or R2 is unsubstituted cycloalkyl then preference is given to C4 to C7 cycloalkyl radicals. Cyclopentyl and cyclohexyl are particularly preferred.

If one of the radicals R1 or R2 is substituted cycloalkyl then preference is given to the above-indicated cycloalkyl radicals, with the substituent or substituents on the cycloalkyl radical possibly being, for example, C1 to C4 alkyl such as methyl, ethyl, propyl, n-butyl or isobutyl, fluoro, chloro, bromo, iodo or C1 to C4 alkoxy, especially methoxy.

If one of the radicals R1 or R2 is aryl or aralkyl then preference is given to phenyl and naphthyl as aryl. Particularly preferred arylalkyl radicals are benzyl and phenylethyl. R1 or R2 may also be substituted aryl radicals if desired. In this case phenyl and naphthyl are preferred and as ring substituents C1 to C4 alkyl, especially methyl, halogen or C1 to C4 alkoxy, especially methoxy.

Typical examples of component (C) include benzenesulfinic acid, sodium benzenesulfinate, sodium benzenesulfinate dihydrate, sodium toluenesulfinate, formamidinesulfinic acid, sodium salt of hydroxymethanesulfinic acid, sodium salt of 2,5-dichlorobenzenesulfinic acid, 3-acetamido-4-methoxybenzenesulfinic acid. Particularly preferred compounds of component (C) are sodium toluenesulfinate or sodium benzenesulfinate and their hydrates.

Other examples of component (C) include a barbituric acid or thiobarbituric acid and/or a barbituric or thiobarbituric acid derivative and/or mixtures thereof of the general structure (IA):

(IA)

wherein X is O or S; and wherein R1, R2, R3, and R4, which may be identical or different, have the following meanings: hydrogen, alkyl (e.g. C1 to C18), substituted alkyl (e.g. C3 to C18), alkenyl (e.g. C2 to C18), cycloalkyl (e.g. C6 to C10), substituted cycloalkyl (e.g. C7 to C18), arylalkyl (e.g. C7 to C18), aryl or substituted aryl radical (e.g. C6 to C18). R1, R2, R3, and R4 may also incorporate a halogen radical such as chloro or a hydroxyl, amino or nitro group.

If one of the radicals R1 to R4 is an unsubstituted alkyl then this radical can be straight-chain or branched and can contain, for example, from 1 to 18 carbon atoms, preferably from 1 to 10, and in particular from 1 to 6 carbon atoms. Examples of low-molecular alkyl radicals are methyl, ethyl, propyl, isopropyl, n-butyl, t-butyl, isobutyl, n-pentyl, and isoamyl.

If one of the radicals R1 to R4 is a substituted alkyl radical then the alkyl moiety of this radical preferably has the number of carbon atoms indicated above for unsubstituted alkyl. If one of the radicals R1 to R4 is alkoxyalkyl or alkoxycarbonylalkyl then the alkoxy radical contains, for example, from 1 to 5 carbon atoms and is preferably methyl, ethyl, propyl, isopropyl, n-butyl, t-butyl, isobutyl, n-pentyl or isoamyl. If one of the radicals R1 to R4 is haloalkyl then the halo moiety is understood to be fluoro, chloro, bromo or iodo.

If one of the radicals R1 to R4 is alkenyl then preference is given to C3 to C5 alkenyl radicals, especially allyl.

If one of the radicals R1 to R4 is unsubstituted cycloalkyl then preference is given to C4 to C7 cycloalkyl radicals. Cyclopentyl and cyclohexyl are particularly preferred.

If one of the radicals R1 to R4 is substituted cycloalkyl then preference is given to the above-indicated cycloalkyl radicals, with the substituent or substituents on the cycloalkyl radical possibly being, for example, C1 to C4 alkyl such as methyl, ethyl, propyl, n-butyl or isobutyl, fluoro, chloro, bromo, iodo or C1 to C4 alkoxy, especially methoxy.

If one of the radicals R1 to R4 is aryl or aralkyl then preference is given to phenyl and naphthyl as aryl. Particularly preferred arylalkyl radicals are benzyl and phenylethyl. R1 to R4 may also be substituted aryl radicals if desired. In this case phenyl and naphthyl are preferred and as ring substituents C1 to C4 alkyl, especially methyl, halogen or C1 to C4 alkoxy, especially methoxy.

Typical examples include barbituric acid, thiobarbituric acid, 1,3,5-trimethylbarbituric acid, 1-phenyl-5-benzylbarbituric acid, 1-benzyl-5-phenylbarbituric acid, 1,3-dimethylbarbituric acid, 1,3-dimethyl-5-phenylbarbituric acid, 1-cyclohexyl-5-ethylbarbituric acid, 5-laurylbarbituric acid, 5-butylbarbituric acid, 5-allylbarbituric acid, 5-hydroxy-5-butylbarbituric acid, 5-phenylthiobarbituric acid, 1,3-dimethylthiobarbituric acid, 5,5-dibromobarbituric acid, trichlorobarbituric acid, 5-nitrobarbituric acid, 5-aminobarbituric acid, 5-hydroxybarbituric acid and 5,5-dihydroxybarbituric acid.

Part B of the kit also comprises a film former as component (D) or as part of component (D).

A film former can generally be described as a substance which—if e.g. applied to a surface—will change from a liquid stage to a solid stage in such a manner as to form a film on the surface.

Thus, the combination of activator and film former in part B of the kit can also be described as an activator contained in a film, wherein the film is typically obtained when a film former is applied to a surface, typically followed by a drying step.

The activator is typically homogeneously dispersed or dissolved in the film.

The molecular weight (Mw) of the film former can vary over a wide range (e.g. from at least about 1000 to about 1,200,000). Typical ranges include from about 10,000 to about 400,000, or from about 20,000 to about 200,000.

If desired, the molecular weight can be determined by GPC technology, using e.g. a polystyrene standard.

If the molecular weight of the film former is too low, the film former might not be able to form a sufficiently durable film or coating. Thus, the effect of a delayed release of the activator might not be obtained. E.g., components like 2-hydroxyethyl acrylate (HEMA), which are classified as film-forming agents in US 2010/0129777, are not suitable as a film former in the sense of the present invention.

The film caused or produced by the film former typically has a thickness in a range from about 0.5 µm to about 100 µm or from about 10 µm to about 50 µm.

Component (D) is typically present in the part B of the kit of parts in an amount of at least about 50 wt.-% or at least about 60 wt.-% or at least about 70 wt.-%.

The amount of component (D) being present in part B of the kit of parts is typically up to about 90 wt.-% or up to about 80 wt.-% or up to about 75 wt.-%.

Typical ranges include from about 50 to about 90 or from about 60 to about 80 or from about 70 to about 75 wt.-%.

Film formers or film forming agents can be classified as natural film former, semi-synthetic film formers, cellulose derivatives, poly(meth)acrylates and vinyl polymers.

Examples of natural film formers include shellac, mastix, sandarac, tolubalsam, dammar resin, benzoe resin, keratin, maizin, gum Arabic and gelatines.

Examples of semi-synthetic film formers include gelatines treated with formaldehyde and salol (acetaldehyde phenol condensate).

Typical cellulose derivatives include cellulose acetate phthalate, hydroxyethylcellulose, hydroxypropylcellulose, methylcellulose, ethylcellulose and hydroxypropylmethyl cellulose phthalate.

Examples of poly(meth)acrylates include copolymers of (meth)acrylic esters and amino functional (meth)acrylates, copolymers of (meth)acrylic acid and methyl methacrylate, polyacrylamide.

Examples of vinyl polymers include polyvinyl pyrrolidon, polyvinyl acetate phthalate (e.g. hydroxypropyl- and hydroxypropyl-methylcellulose), homo- and copolymers of polyvinylacetate, homo- and copolymers of polyvinylpropionate, styrene acrylics, ethylene vinyl acetate, poly(hydroxyethyl methacrylate), poly(vinylethylene glycol acrylate, polyvinyl alcohol(s).

Particular examples for film former(s) include (e.g. fully or partially hydrolyzed) polyvinylalcohol, polymethylvinylether, polyvinylpyrrolidone, (e.g. aqueous) acrylic resin dispersions (e.g. Eudragit™, commercially available from Röhm), gelatine, polysaccharides (e.g. agarose), polyacrylamide, copolymers of vinylpyrrolidinone and acrylamide, hydrophilic cellulose derivatives (e.g. hydroxyethylcellulose, hydroxypropylcellulose, methylcellulose), homo- and copolymers of polyvinylacetate, homo- and copolymers of polyvinylpropionate, styrene acrylics, ethylene vinyl acetate, polyurethanes, hydroxylated acrylates such as poly (hydroxyethyl methacrylate), poly(vinylethylene glycol acrylate), and combinations and mixtures thereof.

The components being contained in part B of the kit are typically present as a film. This film may be located on the surface of a packaging material or the surface of a well of a packaging device or an application instrument or applicator.

The kit may contain further components, which may be present either in part A or part B or in part A and part B.

Components which might be present in addition include
- a solvent or a mixture of solvents as component (E) or part of component (E),
- an adjuvant or a mixture of adjuvants as component (F) or part of component (F),
- a filler or a mixture of fillers as component (G) or part of component (G).

Thus, the kit of parts may contain a solvent. If present, the solvent is typically included in part A of the kit of parts. However, a solvent may also be used when preparing part B of the kit.

Examples of solvents according to component (E) include, but are not limited to linear, branched or cyclic, saturated or unsaturated alcohols, ketones, esters or mixtures of two or more of said type of solvents with 2 to 10 C atoms. Preferred alcoholic solvents include methanol, ethanol, isopropanol and n-propanol.

Other suitable organic solvents are THF, acetone, methylethyl ketone, cyclohexanol, toluene, alkanes and acetic acid alkyl esters, in particular acetic acid ethyl ester.

Generally, it is possible to use the above-mentioned solvents alone or as a mixture of two or more of any of these solvents, if the solvent mixtures do not impair the adhesive properties to such an extent that the desired result cannot be obtained.

If present, component (E) is typically present in an amount of at least about 5 wt.-% or at least about 10 wt.-% or at least about 15 wt.-%.

The amount of component (E) being present in part B of the kit of parts is typically up to about 20 wt.-% or up to about 30 wt.-% or up to about 40 wt.-%.

Typical ranges include from about 5 to about 40 or from about 10 to about 30 or from about 15 to about 20 wt.-% with respect to the weight of the.

The above values refer to the weight of the whole composition being obtained when combining the components being present in part A and part B of the kit.

The composition which can be obtained by combining the components being present in part A and part B of the kit may comprise adjuvants as component (F) or part of component (F).

Typical examples include inhibitors or retarders, stabilizers, pigments, dyes, fluoride release agents, surface tension depressants and wetting aids, antioxidants, and other ingredients well known to those skilled in the art.

The amounts and types of each ingredient in the composition should be adjusted to provide the desired physical and handling properties before and after polymerization. For example, the polymerization rate, polymerization stability, fluidity, compressive strength, tensile strength and durability of the dental material typically are adjusted in part by altering the types and amounts of polymerization initiator(s) and, if present, the loading and particle size distribution of filler(s). Such adjustments typically are carried out empirically based on experience with dental materials of the prior art.

Typical adjuvants include pigments, colorants and/or dyes. Examples include titanium dioxide or zinc sulphide (lithopones), red iron oxide 3395, Bayferrox 920 Z Yellow, Neazopon Blue 807 (copper phthalocyanine-based dye) or Helio Fast Yellow ER. These additives may be used for individual coloring of the dental compositions.

Examples of a photobleachable colorant are Rose Bengal, Methylene Violet, Methylene Blue, Fluorescein, Eosin Yellow, Eosin Y, Ethyl Eosin, Eosin bluish, Eosin B, Erythrosin B, Erythrosin Yellowish Blend, Toluidine Blue, 4',5'-Dibromofluorescein and blends thereof. Further examples of photobleachable colorants can be found in U.S. Pat. No. 6,444,725 and are included herein by reference. The color of the compositions of the present invention may be additionally imparted by a sensitizing compound.

Further additives, which can be added, include stabilizers, especially free radical scavengers such as substituted and/or unsubstituted hydroxyaromatics (e.g. butylated hydroxytoluene (BHT), hydroquinone, hydroquinone monomethyl ether (MEHQ), 3,5-di-tert-butyl-4-hydroxyanisole (2,6-di-tert-butyl-4-ethoxyphenol), 2,6-di-tert-butyl-4-(dimethylamino)methylphenol or 2,5-di-tert-butyl hydroquinone, 2-(2'-hydroxy-5'-methylphenyl)-2H-benzotriazole, 2-(2'-hydroxy-5'-t-octylphenyl)-2H-benzotriazole, 2-hydroxy-4-methoxybenzophenone (UV-9), 2-(2'-hydroxy-4',6'-di-tert-pentyl-phenyl)-2H-benzotriazole, 2-hydroxy-4-n-octoxybenzophenone, 2-(2'-hydroxy-5'-methacryloxyethylphenyl)-2H-benzotriazole, phenothiazine, and HALS (hindered amine light stabilizers). Such adjuvants may optionally comprise reactive functionality so that they will be copolymerized with the resin.

Examples of a fluoride release agent are naturally occurring or synthetic fluoride minerals such as sodium fluoride, fluoride glass such as fluoroaluminosilicate glass, simple and complex inorganic fluoride salts such as potassium zinc fluoride and potassium hexa fluorotitanate, simple and complex organic fluoride salts such as tetra ethyl ammonium tetra fluoroborate or combinations thereof. Optionally these fluoride sources can be treated with surface treatment agents. In certain instances, the fluoride source and the filler (G) can be one and the same.

The composition which can be obtained by combining the components being present in part A and part B of the kit may comprise a filler or a filler matrix as component (G) or part of component (G). The filler matrix can be comprised of one filler or a mixture of different fillers.

The nature of filler of the inventive composition is not particularly limited. The size of the filler particles should be such that a homogeneous mixture with the hardenable component(s) forming the resin matrix can be obtained.

Useful fillers include fumed silica, fillers based on fluoroaluminosilicate glasses, quartz, ground glasses, non-water-soluble fluorides such as $CaF_2$, silica gels such as silicic acid, in particular pyrogenic silicic acid and granulates thereof, cristobalite, calcium silicate, zirconium silicate, zeolites, including the molecular sieves, metal oxide powders, such as aluminium or zinc oxides or their mixed oxides, barium sulphate, yttrium fluoride, calcium carbonate.

The silica is usually dispersed within the resin matrix. The silica particles used in the dental compositions preferably have an average diameter of less than about 200 nm; more preferably, the particles are less than about 100 nm in average diameter. These measurements are preferably based on a TEM (transmission electron microscopy) method, whereby a population is analyzed to obtain an average particle diameter.

The average surface area of the particles is preferably greater than about 15 $m^2/g$ or greater than about 30 $m^2/g$.

Once dispersed in the resin, the particles may be in a discrete (individual) and unassociated (i.e. non-agglomerated, non-aggregated) condition. "Agglomerated" as used herein, is descriptive of a weak association of particles usually held together by charge or polarity and can be broken down into smaller entities. "Aggregated," as used herein, is descriptive of a strong association of particles often bound together by, for example, residual chemicals treatment; further breakdown of the aggregates into smaller entities is very difficult to achieve. If aggregated particles are present, the size of the aggregates is preferably smaller than about 100 to about 200 nm (d50) in order to prevent settling or precipitation of the filler.

Suitable fumed silicas include for example, products sold under the tradename AEROSIL series OX-50, -130, -150, and -200 available from Evonik AG (formerly Degussa AG, Hanau, Germany), and CAB-O-SIL M5 available from Cabot Corp (Tuscola, Ill.).

Useful fluoroaluminosilicate glasses include silanol treated fluoroaluminosilicate glass fillers, as described in U.S. Pat. No. 5,332,429, the disclosure of which is expressly incorporated by reference herein.

For example, a fluoride releasing glass may be added to the dental composition to provide the benefit of long-term release of fluoride in use, for example in the oral cavity.

Optionally, a heavy metal oxide can be included in the dental materials of the invention to provide a radiopaque dental material. It is preferred that the heavy metal oxide be present in an amount effective to impart radiopacity. As used herein, "radiopacity" describes the ability of a hardened dental material to be distinguished from tooth structure using standard dental X-ray equipment in the conventional manner. Radiopacity in a dental material is advantageous in certain instances where X-rays are used to diagnose a dental condition. For example, a radiopaque material would allow the detection of secondary caries that may have formed in the tooth tissue surrounding a filling. The desired degree of radiopacity can be varied, depending upon the particular application and the expectations of the practitioner evaluating the X-ray film.

Oxides of heavy metals having an atomic number greater than about 28 can be preferred. The heavy metal oxide should be chosen such that undesirable colors or shading are not imparted to the hardened resin in which it is dispersed. For example, iron and cobalt would not be favoured, as they impart dark and contrasting colors to the neutral tooth color of the dental material. More preferably, the heavy metal oxide is an oxide of metals having an atomic number greater than 30. Suitable metal oxides are the oxides of yttrium, strontium, barium, zirconium, hafnium, niobium, tantalum, tungsten, bismuth, molybdenum, tin, zinc, lanthanide elements (i.e. elements having atomic numbers ranging from 57 to 71, inclusive), cerium and combinations thereof. Most preferably, the oxides of heavy metals having an atomic number greater than 30, but less than 72 are optionally included in the materials of the invention. Particularly preferred radiopacifying metal oxides include lanthanum oxide, zinc oxide, tin oxide, zirconium oxide, yttrium oxide, ytterbium oxide, barium oxide, strontium oxide, cerium oxide, and combinations thereof. The heavy metal oxide particles may be aggregated. If so, it is preferred that the aggregated particles are less than about 200 nm, and more preferably are less than about 90 nm in average diameter.

In a preferred embodiment the filler matrix comprises a nano-sized filler including nano-sized silica.

Preferred nano-sized silicas are commercially available from Nalco Chemical Co. (Naperville, Ill.) under the product designation NALCO COLLOIDAL SILICAS. For example, preferred silica particles can be obtained from using NALCO products 1040, 1042, 1050, 1060, 2327 and 2329. In a preferred embodiment where the hardenable resin employs a cationic initiation system, the starting silica is preferably acidic (such as Nalco 1042).

Surface-treating the nano-sized silica particles before loading into the dental material can provide a stable dispersion in the resin. "Stable", as used herein, means a dental material in which the particles do not agglomerate after standing for a period of time, such as about 24 hours, under standard ambient conditions, e.g. room temperature (about 20 to about 22° C.), atmospheric pressure, and no extreme electromagnetic forces. Preferably, the surface-treatment stabilizes the nano-sized particles so that the particles will be well dispersed in the hardenable resin and results in a substantially homogeneous composition. Furthermore, it is preferred that the silica be modified over at least a portion of its surface with a surface treatment agent so that the stabilized particle can copolymerize or otherwise react with the hardenable resin during curing.

The silica particles can be treated with a resin-compatibilizing surface treatment agent. Particularly preferred surface treatment or surface modifying agents include silane treatment agents capable of polymerizing with a resin. Preferred silane treatment agent include γ-methacryloxylpropyltrimethoxysilane, available commercially under the trade designation A-174, available commercially from Witco OSi Specialties (Danbury, Conn.) and γ-glycidoxypropyltrimethoxy silane, a product available under the trade designation G6720, available from United Chemical Technologies (Bristol, Pa.).

Alternatively a combination of surface modifying agents can be useful, wherein at least one of the agents has a functional group co-polymerizable with a hardenable resin. For example, the polymerizing group can be ethylenically unsaturated or a cyclic function subject to ring opening polymerization. An ethylenically unsaturated polymerizing group can be, for example, an acrylate or methacrylate, or vinyl group. A cyclic functional group subject to ring opening polymerization generally contains a heteroatom such as oxygen, sulfur or nitrogen, and preferably is a 3-membered ring containing oxygen such as an epoxide. Other surface modifying agents which do not generally react with hardenable resins can be included to enhance dispersibility or rheological properties. Examples of silane of this type include, for example, alkyl or aryl polyethers, alkyl, hydroxy alkyl, hydroxy aryl, or amino alkyl functional silanes.

Upon surface treating the silica particles, they can then be combined with an appropriate hardenable resin to form a dental composition of the invention.

A typical composition which can be obtained by combining the components being present in part A and part B of the kit as described in the text of the invention may comprise the components in the following amounts:

Polymerizable component(s) having an acidic group: from about 2 to about 40 wt.-% or from about 5 to about 30 wt.-% or from about 10 to about 20 wt.-%, Initiator(s): from about 0.5 to about 8 wt.-% or from about 1.0 to about 6 wt.-% or from about 1.5 to about 4 wt.-%, Activator(s): from about 0.05 to about 2.0 wt.-% or from about 0.1 to about 1.0 wt.-% or from about 0.2 to about 0.5 wt.-%, Film Former(s): from about 0.1 to about 5.0 wt.-% or from about 0.2 to about 3.0 wt.-% or from about 0.5 to about 1.0 wt.-%, Solvent(s): from about 5 to about 40 or from about 10 to about 30 or from about 15 to about 20 wt.-%, Adjuvant(s): from about 0 to about 10 wt.-% or from about 1 to about 8 wt.-% or from about 2 to about 6 wt.-%, Filler(s): from about 0 to about 30 wt.-% or from about 5 to about 20 wt.-% or from about 10 to about 20 wt.-%, wt.-% with respect to the weight of the whole composition.

The composition can be obtained by combining (including mixing and kneading) the individual components of the composition, preferably under "safe light" conditions.

The present invention provides a composition (if the components contained in part A and part B of the kit are combined) which can be hardened in an acceptable time frame, e.g., less than about 120 s or less than about 100 s or less than about 60 s, and to a sufficient depth either using visible light source equipment already available in the dental office or electronics fabrication facilities or simply by combining the components under dark light conditions.

The composition obtained by mixing or combining the components is particularly well adapted for use in a wide variety of applications including dental and orthodontic materials, which may be filled or unfilled.

Such materials include direct aesthetic restorative materials (e.g., anterior and posterior restoratives), prostheses, adhesives and primers for oral hard tissues, sealants, cavity liners, orthodontic bracket adhesives for use with any type of bracket (such as metal, plastic and ceramic), crown and bridge cements and the like. These materials are used in the mouth and are disposed adjacent to natural teeth. The phrase "disposed adjacent to" as used herein refers to the placing of a dental material in temporary or permanent bonding (e.g., adhesive) or touching (e.g., occlusal or proximal) contact with a natural tooth. The term "composite" as used herein in the context of a dental material refers to a filled dental material. The term "restorative" as used herein refers to a dental composite that is polymerized after it is disposed adjacent to a tooth. The term "prosthesis" as used herein refers to a composite that is shaped and polymerized for its final use (e.g., as a crown, bridge, veneer, inlay, onlay or the like) before it is disposed adjacent to a tooth. The term "sealant" as used herein refers to a lightly filled dental composite or to an unfilled dental material that is cured after it is disposed adjacent to a tooth.

When the material is applied to a tooth, the tooth can optionally be pre-treated with a primer such as dentin or enamel adhesive by methods known to those skilled in the art.

The invention is also directed to a method of production of the kit.

The method typically comprises the steps of
a) bringing the components contained in part B of the kit in contact with a surface and
b) drying the components applied to the surface to form a film.

These steps can be repeated, if desired. By "surface" is meant a surface of a packaging material or application instrument, not a surface of a tooth.

The application of the components onto the surface can be accomplished by different means. Useful means include coating, spraying, dipping, printing, freeze-drying. This method typically requires the presence of a solvent.

Drying is typically accomplished by letting the volatile components evaporate. Evaporation can be facilitated e.g. by applying a stream of air and/or heat and/or vacuum, e.g. by using a fan.

The obtained film typically contains the activator homogeneously dispersed or dissolved in the film produced by the film former. The obtained film does typically not contain a solvent anymore. Thus, part B of the kit is typically essentially free of solvent.

The thickness of the film is typically within a range from about 0.5 µm to about 100 µm or from about 10 µm to about 50 µm. The thinner the film is, the easier the activator can be dissolved when being combined with the polymerizable monomer being present in part A of the kit.

The surface to which the components are applied can be the surface of an applicator or the surface of a packaging device.

Useful applicators include brushes, sponges, spatulae, and dental instruments such as burnishers or condensers. Specific examples of applicators which can be used are shown in WO 2007/121160, WO 2004/032785 (especially the embodiment shown in FIGS. 1 to 5 and the respective description of the figures), the disclosure of which is explicitly mentioned and herewith incorporated by reference.

Useful packaging devices include blister packages, mixing wells, mixing pads. Specific examples of packaging devices are shown in U.S. Pat. No. 7,097,075, WO 2004/032785 and U.S. Pat. No. 6,105,761, the disclosure of which is explicitly mentioned and herewith incorporated by reference.

So-called single use packages were found to be particularly useful.

The invention is also directed to the use of the kit for the production of a dental composition. Thus, the kit can or is to be used for producing a dental or orthodontic composition or is for use in the dental or orthodontic field.

This process typically comprises the steps of mixing or combining the compositions contained in part A and part B of the kit. The thus obtained mixture or composition is thereafter typically used in the dental or orthodontic field. Such a use typically comprises the steps of
a) placing the composition obtainable by mixing or combining the individual components being present in part A and part B of the kit in contact with the surface of a tooth or orthodontic device,
b) hardening the composition,
wherein between step a) and step b) there can be an optional drying step.

Drying can be accomplished, if desired, by using air, especially pressurized air.

The hardening of the composition mainly depends on the type of initiator(s) used. If the composition contains a light-curing initiator, the hardening reaction is typically initiated by using light of a wavelength in the range from about 200 to about 800. If the composition contains a redox-curing initiator, application of light is typically not required. The hardening reaction typically starts upon combining the activator, initiator and the polymerizable monomer.

Besides part A and part B as described in the text of the invention, the kit may further comprise a part C. Part C may include compositions which can be used in connection with the composition obtainable when combining part A and part B. Those compositions include dental cements, dental filling materials, dental crown and bridge materials, orthodontic adhesives, combinations and mixtures thereof.

Dental cements which can be used include e.g. those described in U.S. Pat. No. 6,982,288 or U.S. Pat. No. 6,939,900. Dental cements are commercially available e.g. under the name RelyX™ Unicem (3M ESPE).

Dental filling materials which can be used include e.g. those described in U.S. Pat. No. 6,030,606 or U.S. Pat. No. 6,387,981. Dental filling materials are commercially available e.g. under the name Filtek™ (3M ESPE).

Dental crown and bridge materials which can be used include e.g. those described in U.S. Pat. No. 7,816,423 Dental crown and bridge materials are commercially available e.g. under the name Protemp™ (3M ESPE).

Orthodontic adhesives which can be used include e.g. those described in U.S. Pat. No. 6,960,079 or U.S. Pat. No. 6,528,555. Orthodontic adhesives are commercially available e.g. under the name Transbond™ (3M Unitek).

Adding a part C to the other two parts might facilitate the whole application process as the individual parts can be adapted to each other with respect to e.g. chemical reactivity. Thus, part C may contain components which may improve the curing reaction of the components which are already present in part A and part B of the kit.

The invention is also directed to a composition which is obtainable when combining or mixing the individual components being present in part A and part B and optionally part C.

The composition is typically stored in a container until use. Depending on the initiator system chosen, various containers can be suitable.

The composition is typically provided as a two-component system.

The following systems were found to be useful:
a) a vial comprising the components of part A and an applicator comprising the components of part B, wherein the activator and film former are contained on a part of the surface of the applicator,
b) a vial comprising the components of part A, a mixing well comprising the components of part B, wherein the activator and film former are contained on a part of the surface of the mixing well and optionally an applicator,
c) a packaging device comprising a compartment I containing the components of part A and separated therefrom a compartment II containing the components of part B, wherein the activator and film former are contained on a part of the surface of the compartment II,
d) a packaging device comprising a compartment I containing the components of part A and separated therefrom a compartment II containing the components of part B, wherein the activator and film former are contained on an applicator located in compartment II.

Figure 1:
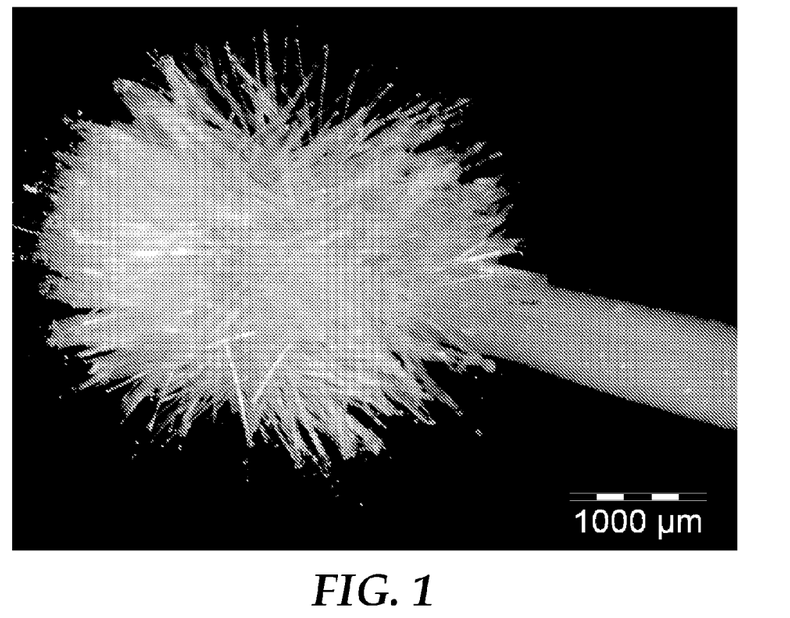
FIG. 1 shows a micrograph of an embodiment according to the invention.

With respect to system c), compartment I is typically sealed against the environment, but can be selectively opened to compartment II via a passage way. Compartment II may comprise an applicator. Compartment II can have the shape of a pocket, that is, being not completely sealed but open to the surroundings in a certain region or section. A particular example is shown in FIG. 1 and the respective description of U.S. Pat. No. 6,105,761 (column 3, line 47 to column 5, line 12).

The volume of the vial or compartment of the packaging device used for storing the components of part A of the kit is typically in the range from about 0.1 to about 20 ml or from about 0.2 to about 10 ml or from about 0.3 to about 5 ml.

One embodiment for a typical application process can be described as follows:
a) providing a packaging device as described in embodiment c) or d) above, wherein e.g. compartment II comprises an removable applicator,
b) transferring the components contained in compartment I to compartment II, thereby bringing the components contained in compartments I and II in contact with each other,
c) optionally using the applicator for mixing the components,
d) removing the applicator from the packaging device,
e) applying the composition being adhered to the surface of the applicator to another surface.

When used in the dental field, the composition is usually applied to the tooth surface in an amount sufficient to etch and prime dental tissue. In this respect the following steps are generally applied:
i) applying the composition to the surface of a tooth (enamel and/or dentin), preferably using a brush or a sponge, the surface of the tooth can be prepared or as it is,
ii) optionally dispersing the composition to a thin film, preferably using a stream of air,
iii) optionally light initiated curing of the composition, the light having a wave length in range of e.g. about 300 nm to about 800 nm, and
iv) optionally applying a dental filling composition, cement, bracket adhesive, core build-up material or sealant.

One or more of the above described process steps might also be subject of an instruction for use, which may be a further part of the kit.

FIG. 1 shows a micrograph of an embodiment according to the invention. What can be seen is an applicator brush having a handle for grasping the device and bristles located at one end of the handle. The bristles are coated with an initiator component dissolved or dispersed in a film former.

Figure 2:
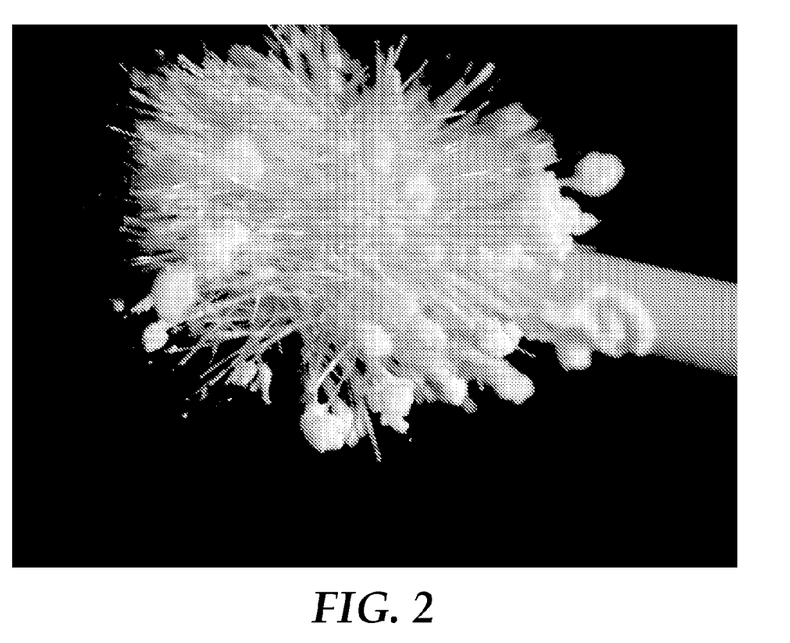
FIG. 2 shows a micrograph of an applicator brush according to the prior art.

FIG. 2 shows a micrograph of an applicator brush according to the prior art. What can be seen is an applicator brush having a handle for grasping the device and bristles located at one end of the handle. On the surface of the bristles an initiator component is attached in granular form.

A dental composition according to the invention does not necessarily comprise halogenated or aromatic solvents and/or solvents with a boiling point larger than about 150° C., aldehydes, intensely coloured dyes or pigments which are not photobleachable, fillers with an average particle size larger than about 50 µm, non-agglomerated fillers with a particle size of less about than 20 nm.

In this context "essentially free from" means that the content is typically below about 1 wt.-% or below about 0.5 wt.-% or below about 0.1 wt.-% with respect to the whole composition.

EXAMPLES

Unless otherwise indicated, all parts and percentages are on a weight basis, all water is deionized water, and all molecular weights are weight average molecular weight. Moreover, unless otherwise indicated all experiments were conducted at ambient conditions (about 23° C.; about 50% relative humidity). Moreover, nearly all process steps are conducted under an atmosphere of dry air.

Measurements

Particle Size

If desired, the mean particle size can be determined using a commercially available granulometer (Laser Diffraction Particle Size Analysis Instrument, MASTERSIZER 2000; Malvern Comp.) according to the instruction of use provided by the manufacturer.

Viscosity ($\eta$)

If desired, the viscosity can be measured with a Haake RotoVisco RV1 device (rotor C60/1 for viscosities up to 8000 mPas or rotor C20/1 for viscosities above 8000 mPas together with stator P61). The viscosity is typically measured at 23.0° C. between two plane and parallel plates (i.e. stator and rotor). After activation and rectification of the system, the appropriate rotor is installed. Then the rotor is lowered and the distance between stator and rotor is adjusted to 0.052 mm (using Software RheoWin Pro Job Manager Software Version 2.94) for the viscosity measurement. Then the rotor is lifted and the material to be measured is given onto the stator (1.0 ml with rotor C60/1 or 0.04 ml with rotor C20/1). Without undue delay, the rotor is lowered into the preliminary adjusted measuring position. The material to be measured is tempered at 23.0° C. The shear rate for the measurement has to be adjusted to a value that the torque is at least 5000 µNm (therefore normally shear rates of 100, 200, 500, or 1000 s$^{-1}$ are used depending on the viscosity of the material to be measured). The measurement is started and run for 60 s. The viscosity values (Pas) are recorded starting 20 s after the start of measurement and the mean value of the recorded values is given as viscosity.

The name and description of the components or devices used are given in Table 1.

TABLE 1

| Name | Description |
| --- | --- |
| Microbrush ™ | Application device |
| sodium toluene sulfinate | Activator |
| Polyvinyl alcohol | Film former |
| Adper ™ Easy Bond | Bonding composition containing polymerizable components with acidic group(s) (commercially available from 3M ESPE) |
| Scotchbond ™ Etchant | Etchant (commercially available from 3M ESPE) |
| RelyX ™ ARC resin cement | Resin cement (commercially available from 3M ESPE) |

Inventive Example

Microbrushes™ (Size M) were dipped into a solution of 1 wt.-% sodium toluene sulfinate and 0.25 wt.-% hydrolyzed polyvinyl alcohol (M=72.000) in deionized water. Then the brushes were allowed to dry in an oven at about 70° C. for about 1.5 h.

Comparative Example 1

Microbrushes™ (Size M) were dipped into a solution of 1 wt.-%% sodium toluene sulfinate in deionized water. Then the brushes were allowed to dry in an oven at about 70° C. for about 1.5.

Application Example

Four drops of Adper™ Easy Bond (3M ESPE) were dispensed in a well. Adper™ Easy Bond is commercially available from 3M ESPE company and contains inter alia a polymerizable monomer having an acid group in the molecule.

The sulfinate coated brush was dipped into Adper™ Easy Bond and applied liberally for 20 s to the exposed dentin surface of a bovine tooth potted in acrylic resin, that had previously been etched with Scotchbond™ Etchant (3M ESPE) for about 15 s. Then the adhesive was dried with pressurized air for about 5 s. This procedure was repeated consecutively with the same brush for a total of 5 times.

Then RelyX™ ARC resin cement (3M ESPE) was applied to the underside of sandblasted, silane treated stainless steel cylinders (4 mm diameter). The cylinders were placed on the Adper™ Easy Bond layer for about 10 min, while a load of 250 g was exerted on each of them at about 36° C.

Then the teeth with the cylinders cemented to them were stored at 100% relative humidity at about 37° C. for about 24 h. After this time, bond strength was measured in shear mode using a Zwick Z010 universal testing machine (crosshead speed 2 mm/min), see Table 2 showing the shear bond strength values in MPa.

TABLE 2

| Activator brush | Tooth #1 | Tooth #2 | Tooth #3 | Tooth #4 | Tooth #5 |
| --- | --- | --- | --- | --- | --- |
| Inv. Example | 40.2 | 39.4 | 40.6 | 52.4 | 50.1 |
| Comp. Example 1 | 49.6 | 37.1 | 28.5 | 16.7 | 1.9 |

As can be seen, high level bond strength values for 5 consecutively treated teeth can be achieved, if a kit according to the invention has been used.

The invention claimed is:

1. A kit of parts comprising part A and part B, part A comprising:
    at least one polymerizable component with an acid group, wherein the at least one polymerizable component is present in an amount from about 5 to about 20 wt.-%,
    an initiator or an initiator system, wherein the initiator or the initiator system is present in an amount from about 1 to about 5 wt.-%, part B comprising:
    at least one activator, wherein the activator is present in an amount from about 0.1 to about 0.5 wt.-%, and
    at least one film former with a molecular weight of at least about 1,000, wherein the film former is present in an amount from about 0.2 to about 1.5 wt.-%, and wherein the at least one film former is located
        on the surface of an applicator or packaging material, or
        on the surface of a well of a packaging device,
    and further wherein the activator is dissolved or dispersed in the film former;
the kit further comprising at least one of the following components, contained in part A, part B, or part A and part B, comprising:
    one or more solvents, wherein the one or more solvents are present in an amount from about 5 to about 20 wt.-%,
    one or more adjuvants, wherein the one or more adjuvants are present in an amount from about 0 to about 1 wt.-%,
    one or more fillers: wherein the one or more fillers are present in an amount from about 0 to about 20 wt.-%,
wherein wt.-% is with respect to the weight of the whole composition.

2. The kit according to claim 1, wherein the polymerizable component of part A comprises a polymerizable moiety selected from an acrylate, (meth)acrylate, epoxy-functional moiety and combinations thereof, and wherein the acid group is selected from a carboxylic acid, phosphoric acid, sulphonic acid moiety and combinations thereof.

3. The kit according to claim 1, wherein the initiator or initiator system comprises at least one of the following elements: oxidizing agent, a reducing agent, a sensitizing agent, onium salt, electron donor or a combination of two or more of these elements.

4. The kit according to claim 1, wherein the activator comprises at least one of the following moieties: barbituric acid, barbituric acid salt, thiobarbituric acid, thiobarbituric acid salt, sulfinic acid, sulfinic acid salt or sulfinic acid ester.

5. The kit according to claim 1, wherein the film former is selected from the group consisting of natural film formers, semi-synthetic film formers, cellulose derivatives, poly (meth)acrylates, vinyl polymers, polyurethanes, mixtures and combinations thereof.

6. The kit according to claim 1, the thickness of a film produced by the film former being in a range from about 0.5 µm to about 100 µm.

7. The kit according to claim 1, wherein the components of part A and part B are mixed to produce an adhesive composition.

8. The kit according to claim 7, wherein the adhesive composition is suitable to be applied to the surface of a tooth or wherein the adhesive composition is a dental adhesive.

9. The kit according to claim 1, further comprising a part C, part C being selected from a dental cement, a dental filling material, a dental crown or dental bridge, a dental sealant, a dental core build-up material, an orthodontic adhesive and combinations and mixtures thereof.

10. A method for producing the kit as described in claim 1, the method comprising the steps of:
   bringing the components contained in part B of the kit in contact with a surface,
   drying the surface to form a film.

11. The kit according to claim 1, wherein part A is not in contact with part B.

* * * * *

UNITED STATES PATENT AND TRADEMARK OFFICE
CERTIFICATE OF CORRECTION

| | | |
|---|---|---|
| PATENT NO. | : 9,498,313 B2 | Page 1 of 1 |
| APPLICATION NO. | : 13/812588 | |
| DATED | : November 22, 2016 | |
| INVENTOR(S) | : Christoph Thalacker | |

It is certified that error appears in the above-identified patent and that said Letters Patent is hereby corrected as shown below:

On the Title Page

Column 1 (PCT Publication Date)
Line 1, delete "Feb. 2, 2013" and insert -- Feb. 2, 2012 --, therefor.

In the Specification

Column 15
Line 38, delete "Neazopon" and insert -- Neozapon --, therefor.

Signed and Sealed this
Fifteenth Day of August, 2017

Joseph Matal
*Performing the Functions and Duties of the*
*Under Secretary of Commerce for Intellectual Property and*
*Director of the United States Patent and Trademark Office*